United States Patent
Sonnemans et al.

(10) Patent No.: US 8,611,629 B2
(45) Date of Patent: Dec. 17, 2013

(54) VESSEL ANALYSIS

(75) Inventors: Jeroen J. Sonnemans, Eindhoven (NL); Raymond J. Habets, Eindhoven (NL); Javier Olivan Bescos, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 245 days.

(21) Appl. No.: 13/132,938

(22) PCT Filed: Dec. 3, 2009

(86) PCT No.: PCT/IB2009/055484
§ 371 (c)(1),
(2), (4) Date: Jun. 6, 2011

(87) PCT Pub. No.: WO2010/067276
PCT Pub. Date: Jun. 17, 2010

(65) Prior Publication Data
US 2011/0235891 A1    Sep. 29, 2011

(30) Foreign Application Priority Data
Dec. 10, 2008  (EP) .................................... 08171149

(51) Int. Cl.
*G06K 9/00*   (2006.01)
(52) U.S. Cl.
USPC ......................................................... 382/131
(58) Field of Classification Search
USPC .......................... 382/128–134; 128/920–925; 356/39–49; 600/407–414, 424–426; 345/581–618
See application file for complete search history.

(56) References Cited

U.S. PATENT DOCUMENTS

| | | |
|---|---|---|
| 5,768,405 A | 6/1998 | Makram-Ebeid |
| 2001/0044576 A1 | 11/2001 | Vining |
| 2003/0031351 A1* | 2/2003 | Yim ............................... 382/130 |
| 2005/0110791 A1 | 5/2005 | Krishnamoorthy et al. |
| 2007/0024617 A1* | 2/2007 | Poole ........................... 345/424 |
| 2007/0031019 A1 | 2/2007 | Lesage et al. |
| 2007/0160274 A1 | 7/2007 | Mashiach |
| 2007/0291230 A1* | 12/2007 | Yamaguchi et al. .......... 351/221 |
| 2008/0095423 A1 | 4/2008 | Redel et al. |
| 2008/0101667 A1 | 5/2008 | Begelman et al. |

FOREIGN PATENT DOCUMENTS

| WO | 2006000953 A1 | 1/2006 |
|---|---|---|
| WO | 2006055031 A2 | 5/2011 |

OTHER PUBLICATIONS

Kirbas, C., et al.; A Review of Vessel Extraction Techniques and Algorithms; 2004; ACM Computing Surveys; 36(2) 81-121.

Sun, Y.; Automated Identification of Vessel Contours in Coronary Arteriograms by an Adaptive Tracking Algorithm; 1989; IEEE Trans. On Medical Imaging; 8(1)78-88.

* cited by examiner

*Primary Examiner* — Atiba O Fitzpatrick

(57) ABSTRACT

A system for performing vessel analysis uses display means (1) for displaying a three-dimensional image representing at least a tubular structure. Indicating means (2) are used for enabling a user to indicate a position on a vessel of the tubular structure, for obtaining an indicated position. Identifying means (3) are used for identifying a portion of the tubular structure situated around the indicated position, including any bifurcations, and extending up to a predetermined distance measure from the indicated position, for obtaining an identified portion. The display means (1) is also used for displaying a graphical annotation in the displayed three-dimensional image, indicative of the identified portion of the tubular structure.

20 Claims, 1 Drawing Sheet

VESSEL ANALYSIS

FIELD OF THE INVENTION

The invention relates to analysis of a tubular structure, in particular one or more vessels of a tubular structure in a medical image. The invention also relates to user interaction with a vessel analysis tool.

BACKGROUND OF THE INVENTION

Medical image datasets include medical images of vascular structures. These medical images may be two-dimensional (such as in vascular x-ray), or three-dimensional (such as in CT angiography or MR angiography). The three-dimensional image may be a volumetric image, which means that vascular structures are represented in terms of gray values. Vessel tracking tools exist that can identify parts of the vascular structure, based on these gray values.

For example, US 2008/0101667 A1 discloses a device for presenting information associated with a blood vessel to a user for assessment of the blood vessel. The device includes a memory, the memory being capable of storing imaging data defined in three dimensions, and a processor operably coupled to the memory to receive the imaging data. The processor is configured to present a two-dimensional slice of three-dimensional imaging data of a blood vessel to a user in a first user interface; to receive a blood vessel selection from the user, wherein the user selects the blood vessel through an interaction with the first user interface; to identify a blood vessel path associated with the received blood vessel selection from the three-dimensional imaging data; and to present an intensity of the selected blood vessel along the identified blood vessel path to the user for analysis of the selected blood vessel.

SUMMARY OF THE INVENTION

It would be advantageous to have an improved system for performing vessel analysis. To better address this concern, in a first aspect of the invention a system is presented that comprises display means for displaying a three-dimensional image representing at least a tubular structure;

indicating means for enabling a user to indicate a position on a vessel of the tubular structure, for obtaining an indicated position; and identifying means for identifying a portion of the tubular structure situated around the indicated position, including any bifurcations, and extending up to a predetermined distance from the indicated position, for obtaining an identified portion.

The user only needs to indicate a single point on the vascular structure. Following this, the system identifies a portion of the tubular structure in a predictable and consistent way. Since the identified portion contains the full tubular structure, including any bifurcations, there are no surprises as to which vessel will be identified. This increases the user's confidence when indicating a position. Also, because the vessel is identified up to a predetermined distance, there is no need to indicate any end point of the vessel segment to be analyzed. The system provides an efficient tool for performing vessel analysis of a portion of a vascular structure.

The display means may be arranged for displaying a graphical annotation in the displayed three-dimensional image, indicative of the identified portion of the tubular structure. This provides a feedback to the user of the identified portion, allowing the user to verify the identified portion. The user may, for example, thereafter indicate another point on the vascular structure, after which the identifying means can identify a corresponding portion of the tubular structure. The reproducible way in which the portion of the tubular structure is identified makes the displayed graphical annotation also reproducible. Such annotation may also be stored in a patient file.

The identifying means may comprise measuring means for measuring the predetermined distance along the tubular structure. This is a suitable way of measuring the predetermined distance, taking into account the shape of the vessels. The identified portion may include the vessels from the indicated position up to an end position on the vessel, the length of the vessel from the indicated position to the end position being substantially equal to the predetermined distance. Alternatively, the Euclidean distance may be used.

The measuring means may be arranged for measuring a length of the tracked vessel from the indicated position along the tubular structure. Keeping the length of the tracked vessel constant is an efficient way to make the vessel tracking consistent.

The measuring means may be arranged for establishing a number of bifurcations encountered from the indicated position along the tubular structure. This is another way to make the vessel tracking consistent.

Reformat means may be arranged for providing a multi-curved reformat following the curvature of at least a part of a vessel from the indicated position up to and beyond a bifurcation of the tubular structure, and following the curvature of at least part of two vessels beyond the bifurcation. This visualization mode provides a useful view of the bifurcation.

The indicating means may be arranged for being responsive to a mouse move event. The mouse move event makes it possible to very efficiently identify some portions of the vascular structure by moving the mouse cursor over the vessel positions of interest. Each time a mouse move event is detected, the identifying means and/or display means may be activated to provide an updated identified portion.

The system may comprise estimation means for estimating a local tracking parameter from the volumetric image at the indicated position after the user has indicated the position. This allows initializing a vessel tracking algorithm with a local tracking parameter. This initializing step allows the vessel tracking tool to be used with a wide range of vessels.

The estimation means may be arranged for computing a weighted average of an element of a structure tensor, the weighted average being computed over a region of a given size around the indicated position. Such a weighted average of an element of a structure tensor may be used as an element of an averaged structure tensor. The averaged structure tensor may be used to establish the orientation of the vessel at the indicated position.

A medical imaging workstation may comprise the system set forth.

A method of performing vessel analysis may comprise:

displaying a three-dimensional image representing at least a tubular structure;

enabling a user to indicate a position on a vessel of the tubular structure, for obtaining an indicated position; and identifying a portion of the tubular structure situated around the indicated position, including any bifurcations, and extending up to a predetermined distance measure from the indicated position, for obtaining an identified portion.

A computer program product may comprise instructions for causing a processor system to perform the method set forth.

It will be appreciated by those skilled in the art that two or more of the above-mentioned embodiments, implementations, and/or aspects of the invention may be combined in any way deemed useful.

Modifications and variations of the image acquisition apparatus, of the workstation, of the system, and/or of the computer program product, which correspond to the described modifications and variations of the system, can be carried out by a person skilled in the art on the basis of the present description.

A person skilled in the art will appreciate that the method may be applied to multidimensional image data, e.g., to 2-dimensional (2-D), 3-dimensional (3-D) or 4-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will be further elucidated and described with reference to the drawing, in which.

DETAILED DESCRIPTION OF EMBODIMENTS

In some vascular applications, one of the goals is to visualize vessels by using curved planar or straightened reformat views. Also, local vessel parameters may be measured, such as area and radius, at several locations in the image data, for example to quantify the degree of stenosis or the size of an aneurysm. These visualization techniques may use a path through the vessel center. Automatic path tracking tools are often limited to only a few vessels. Semi-automatic path tracking tools may need input from a user to indicate either a single-point tracking or two points on the vessel. When only a single input point is used, the user has no control over the length of the tracked path or the vessel that is tracked. Tools that use a start point and an end point given by the user have the drawback that they need more user input. Also, if the user places the points too far apart or in different vessels, either the path result is wrong or the computation time is too long. Some vessel tracking tools need to first segment a vessel structure before tracking a centerline through it. This may not be efficient.

The interaction may be improved by using a tracking tool offering a different interaction possibility. Using an arbitrary visualization, a user can point at any location on the vascular structure (for example by moving the mouse cursor over the image) and the algorithm may track a local tree automatically and interactively. This tracking may be performed up to a maximum vessel length. The interaction methods described herein enable a redefinition of the paradigm of vascular inspection. The algorithm is able to give a user a preview of what the effect would be of selecting a certain vessel in a kind of "What if I clicked here?" way. The interaction methods described herein can be directly linked to a wide variety of visualization and quantification techniques.

By making sure that the tracking of a vessel portion and the visualization of the tracked vessel portion are fast operations, interactivity may be improved. As only a limited part of the vessel tree is tracked, the tracking is made quicker. Path or tree-based visualizations and measurements can be performed anywhere with only limited interaction. By providing visualization feedback, a direct response to a user's action is shown, which makes the tool easier to understand and to learn. The behavior of the tool may be more predictable for a user, because the length of the tracked vessel portion may be independent of the mouse location. This gives a predictable and understandable result when the mouse is moved along a vessel. The techniques described herein can be applied, for example, in applications for multi-modality 3D vascular analysis. These tools offer advanced viewing, segmentation, inspection and quantification of vessels.

Figure 1:
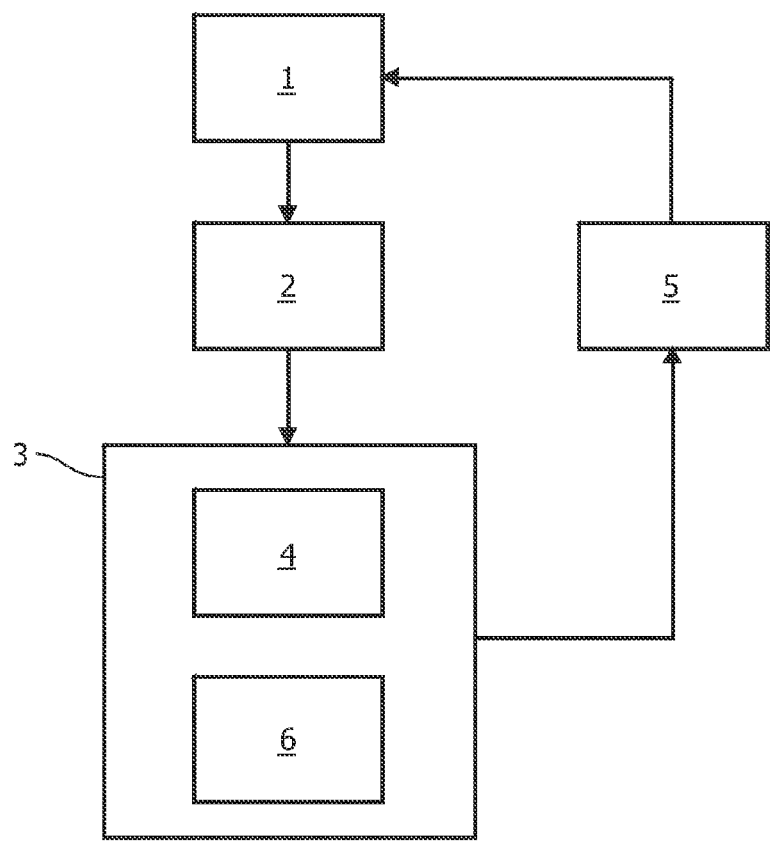
FIG. 1 shows a block diagram of a system for performing vessel analysis.

The term 3D vascular quantification may refer to a collection of applications, which target different vascular structures, using different acquisition methods, but for which the requirements for the desired measurements may be similar. Anatomical examples are the aorta, the carotid arteries, the coronary arteries, the peripheral leg arteries and the coronary arteries. MR and CT and rotational X-ray are examples of modalities used to acquire image data of said anatomical structures. An example of vascular inspection would be to look for widened or obstructed parts of a vessel. A more particular example would be to search for pulmonary embolisms in the lung arteries. Vascular applications can visualize vessels, using advanced visualization techniques for inspection purposes such as curved MPR. These applications can also measure local vessel parameters such as the area and radius of a vessel at several locations in the image data to quantify the degree of stenosis or the size of an aneurism. These measurements can be performed on a cross-section through the vessel of interest which can be generated automatically, or by navigating along a vessel centerline. Other applications may focus on surgical planning of vascular interventions such as stent planning FIG. 1 shows a block diagram of a system for performing vessel analysis. The system may be built up of a number of blocks. Each block may be partially or completely implemented in software. The system may further comprise (not shown): a processor, storage means, a display, user input means such as a keyboard and/or a mouse, a communication port. The processor may be arranged for executing instructions that are part of a vessel analysis tool. The storage means may comprise a RAM, a ROM, a hard disk, removable media such as CD and DVD. The storage means can be used for storing the computer instructions and/or for storing medical image data. The input means can be used for enabling a user to indicate a position in the tubular structure. Moreover, the input means can be used for enabling a user to control the system. The communication port can be used for communicating with another computer system, for example a server. The communication port can be arranged for being connected to a network such as a local area network, wide area network, and/or the Internet. The other computer system may be reached via the network for retrieving image data, and for transmitting vessel analysis reports, for example.

Display means 1 may be provided for displaying a three-dimensional image representing at least a tubular structure. This three-dimensional image has been obtained via the communication port and may be stored in the storage means. Different kinds of visualization may be used to display the image. For example, direct volume rendering, maximum intensity projection, or a slice view may be displayed. Multiple kinds of rendering may be employed sequentially or simultaneously. The system may allow the image to be zoomed, panned, and/or rotated in order to obtain a proper view of the image. The image may represent a tubular structure, for example the image comprises volume elements (voxels) indicative of gray values at particular coordinate locations of the volume. Vessel structures may be recognized by their particular shape and, in some cases, by their gray values. A three-dimensional image may also represent a vascular structure as a surface model, for example.

Indicating means 2 may be provided for enabling a user to indicate a position on a vessel of the tubular structure, for obtaining an indicated position. Such indicating means may be realized by enabling a user to position the mouse cursor on a position in the displayed image. Based on the mouse cursor position, the position on the vessel can be computed in a way known in the art as such.

Identifying means 3 may be provided for identifying a portion of the tubular structure situated around the indicated position, including any bifurcations, and extending up to a predetermined distance measure from the indicated position, for obtaining an identified portion. The identifying means 3 may be arranged for being operative in response to a mouse move event, for example.

The display means 1 may be arranged for displaying a graphical annotation in the displayed three-dimensional image, indicative of the identified portion of the tubular structure. For example, the vessel centerline is drawn in a distinguishable color.

The identifying means 3 may comprise measuring means 4 for measuring the predetermined distance measure along the tubular structure. For example, a wavefront algorithm is applied to track the vessel, every new wave adding a predetermined amount to the measured distance. The identifying means 3 identifies the tubular structure up to the predetermined distance. An alternative is to measure the Euclidean distance. The measuring means 4 may be arranged for measuring a length of the tracked vessel from the indicated position along the tubular structure. For example, a wavefront algorithm is applied to track the vessel, every new wave adding a predetermined amount to the measured distance. The identifying means 3 identifies the tubular structure up to the predetermined distance. Alternatively, the measuring means 4 may be arranged for establishing a number of bifurcations encountered from the indicated position along the tubular structure. For example, the vessels are identified from the indicated position up to the second bifurcation.

Reformat means 5 may be capable of providing a multi-curved reformat (a multi-curved MPR). The curvature of the reformat corresponds to the curvature of at least a part of a vessel from the indicated position up to and beyond a bifurcation of the tubular structure, and follows the curvature of at least part of two vessels beyond the bifurcation. The reformat may be shown on the display 1.

The indicating means 2 may be arranged for being responsive to a mouse move event. This is convenient, in particular when the vessel tracking is performed sufficiently quickly. Vessels can be explored without having to explicitly click at certain positions. In addition to said responsiveness of the system to a mouse move event, the identification and annotation of the vessel structure up to a predetermined distance from the indicated position further increases the usability of the system.

The three-dimensional image may comprise a volumetric image, the identifying means 3 further comprising estimation means 6 for estimating a local tracking parameter from the volumetric image at the indicated position in response to the user indicating the position. By estimating the local tracking parameter directly from the volumetric image (i.e., the gray values of the voxels) in response to the user indicating the position, it is possible to adapt to different vascular regions, which allows using the system without first selecting a particular kind of vessel.

The estimation means 6 may be arranged for computing a weighted average of an element of a structure tensor, the weighted average being computed over a region of a given size around the indicated position. This is an effective, general way of initializing the tracking algorithm, which is applicable to a large variety of vascular structures. This tensor can be computed quickly. It is not necessary to track the vascular structure beforehand, this can be done after the user has indicated the position.

The system of FIG. 1 may be incorporated in a medical imaging workstation or in a console of a medical imaging apparatus. A person skilled in the art will understand that the medical imaging workstation and the console comprise at least one processing unit and memory. It may further comprise many other units, e.g. disk drives, RAMs, caches, displays, data and instruction buses, displays, and keyboards.

Figure 2:
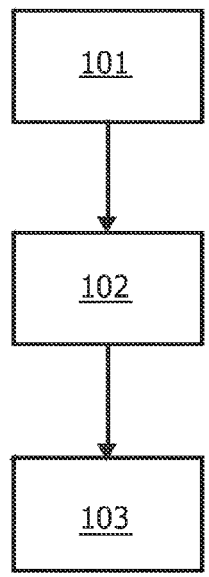
FIG. 2 shows a block diagram of a method of performing vessel analysis.

FIG. 2 illustrates a method of performing vessel analysis. The method comprises, in step 101, displaying a three-dimensional image representing at least a tubular structure. In step 102, a user is enabled to indicate a position on a vessel of the tubular structure, for obtaining an indicated position. In step 103, a portion of the tubular structure around the indicated position is identified. The portion may include any bifurcations and may extend up to a predetermined distance measure from the indicated position, for obtaining an identified portion.

For inspection of a vessel, the user can visualize the data with path geometry-independent visualization techniques such as multi-planar reformat (MPR), a Maximum Intensity Projection (MIP) or a volume rendering (VR). For path-based visualization techniques, a path through the vessel center is required.

An algorithm for tracking a tree may be provided. Here, the word "tree" refers to at least part of a vascular structure, including bifurcations and side branches. Such an algorithm may find the local tree topology starting from a 3D arbitrary position in the data (for example, a user selected position). In the tree topology it is possible to encode the coordinates of each vessel, the relation between vessels and the position of each bifurcation. Tree extraction may be limited by a maximum vessel tracking length. This length may be measured along the tracked vessels rather than in a straight line.

The mouse location on an arbitrary visualization of a 3D medical image may be translated to the {x, y, z} data position. For example, the {x, y, z} position corresponding to a vessel which is visible under the mouse cursor may be used. Using a centering algorithm, the local vessel center point may be computed and the tree may be tracked from this position using a maximum vessel length criterion. Using the tracked tree, a tree- or path-based visualization can be created and measurements can be computed. If the user is satisfied with the result, he can "dock"/finalize the tracking result. For example, the tracking result can be finalized by means of a single mouse click. After this, a user can decide to edit the tracking result. Once the user is satisfied, the resulting images and corresponding measurement results can be sent to a reporting tool.

In an implementation example, a "tree probe" functionality may be activated with a button on the task panel. After activation of the "tree probe", by moving the mouse over the image the tree is tracked automatically up to a given distance. An orthoview is aligned at the mouse location, based on the local tree direction. Bifurcations may be marked in the image, for example by using a different color. Instead of the orthoview it is also possible to create and display curved planar reformats (at the location of the longitudinal views). Moreover, a multi-planar reformatted (MPR) view may be aligned with the nearest bifurcation, taking into account the three vessel segments departing from the bifurcation.

A method may be provided for tracking, from a user-defined mouse location and over a given maximum vessel length, a local tree topology where the exact position of each bifurcation and vessel is known, with full interactivity and maximum reproducibility in an arbitrary visualization of 3D medical image data without requiring any mouse clicks. The tree topology may be used to interactively show a visualization which is based on the tree topology such as a curved MPR, a multi-curved MPR, a straightened reformat, an ortho-view, a highlighted volume rendering etc. A vessel edge detection method may be used along the local tree topology for computation of quantification parameters such as area, diameter and radius and for visualization of these parameters on all available views. Automatic measurement locations may be proposed for quantification and other diseases, based on automatically derived parameters. Information such as images and measurements can be sent to a report tool with only one mouse click.

Vessel tracking systems may be initialized by choosing preset values specific for a particular application. For example, the presets are specific to a vascular region (for example 'peripheral vessels', or 'coronary arteries') and/or imaging modality (for example CT).

However, it is also possible to add a local parameter estimation algorithm (preferably real-time) that initializes the tracking parameters (and optionally updates the parameters during tracking). This allows inspection without imposing assumptions on particular vessel dimensions. It allows the tracking tool to track vessels having a wide range of diameters. Also, the initialization of tracking parameters allows the inspection to be performed on MR images where the intensity values of vessels are not known beforehand (and a lot of inhomogeneity artifacts may exist). Given a 3D source data volume of a vascular structure, the user can select a visualization like MIP (maximum intensity projection), MPR (multi-planar reformat) or volume rendering. To indicate a position on the vessel structure, the user can inspect the visualization by moving the mouse over the image. The following steps may be taken for initializing the vessel tracking at an indicated position: retrieving coordinates $\{x, y, z\}$ of indicated positions in a 3D source volume; computing the local vessel orientation. Also, the vessel contour may be computed, taking account of the local vessel orientation.

The local vessel orientation may be found by establishing the image structure orientation; the latter may be computed directly from the local image gray-scale values, using the structure tensor. The structure tensor may be given by $$J = \begin{bmatrix} \langle g_x g_x \rangle & \langle g_x g_y \rangle & \langle g_x g_z \rangle \\ \langle g_y g_x \rangle & \langle g_y g_y \rangle & \langle g_y g_z \rangle \\ \langle g_z g_x \rangle & \langle g_z g_y \rangle & \langle g_z g_z \rangle \end{bmatrix}$$

Here $g_i$ is the image gradient in the direction i. The brackets $\langle \rangle$ denote a weighted average over a region of a given size. The weighting operation may be carried out using Gaussian blurring. After the structure tensor has been computed, the eigenvalues $\{\lambda_0, \lambda_1, \lambda_2\}$ and eigenvectors $\{v_0, v_1, v_2\}$ may be computed. The eigenvalues may be sorted using the convention $\lambda_0 \leq \lambda_1 \leq \lambda_2$. Therefore, $v_0$ corresponds to the direction in which the weighted product of the gradient is minimal. In a tubular structure this corresponds to the local vessel direction. $v_1$ and $v_2$ span the cross-section plane perpendicular to the vessel.

Using the structure tensor, the local vessel direction may be established. An estimation of the vessel lumen cross section perpendicular to this vessel direction can be established. For example, a circular cross section may be established, or a more detailed contour detection may be performed. The image intensities inside the vessel cross section and outside the vessel cross section can be compared. Such a comparison may be used to initialize or update parameters of the tracking algorithm.

It will be appreciated that the invention also extends to computer programs, particularly computer programs on or in a carrier, adapted for putting the invention into practice. The program may be in the form of a source code, an object code, a code intermediate source and object code, such as a partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the program is embodied in such a signal, the carrier may be constituted by such a cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for performing vessel analysis, comprising
   a display device that displays a three-dimensional image representing at least a tubular structure;
   a selector device that enables a user to indicate a position on a vessel of the tubular structure, to select an indicated position; and
   a processor that identifies a portion of the tubular structure based on the indicated position,
   wherein the identified portion includes bifurcations, if any bifurcations exist in the portion, and extends up to a predefined distance measure from the indicated position without further user input, the predefined distance measure being independent of the image and the indicated position.

2. The system according to claim 1, wherein the display device displays a graphical annotation in the displayed three-dimensional image, indicative of the identified portion of the tubular structure.

3. The system according to claim 1, wherein the processor measures the predefined distance measure along the tubular structure.

4. The system according to claim 3, wherein the processor measures a length of the tracked vessel from the indicated position along the tubular structure.

5. The system according to claim 3, wherein the processor counts a number of bifurcations encountered from the indicated position along the tubular structure.

6. The system according to claim 1, wherein the processor provides a multi-curved reformat following the curvature of at least a part of a vessel from the indicated position up to and beyond a bifurcation of the tubular structure, and following the curvature of at least part of two vessels beyond the bifurcation.

7. The system according to claim 1, wherein the selector device is responsive to a mouse move event.

8. The system according to claim 1, wherein the three-dimensional includes a volumetric image, and the processor estimates a local tracking parameter from the volumetric image at the indicated position in response to the user indicating the position.

9. The system according to claim 8, wherein the processor computes a weighted average of an element of a structure tensor, the weighted average being computed over a region with a given size around the indicated position.

10. A medical imaging workstation comprising the system according to claim 1.

11. A method of performing vessel analysis, comprising
    displaying, on a display device, a three-dimensional image representing at least a tubular structure;
    enabling a user to indicate a position on a vessel of the tubular structure displayed on the display device to provide for obtaining an indicated position; and
    identifying, by a processing system, a portion of the tubular structure situated around the indicated position,
    wherein the identified portion of the tubular structure includes bifurcations, if any bifurcations exist in the portion, and extends up to a predefined distance measure from the indicated position without further user input, the predefined distance measure being independent of the image and the indicated position.

12. The method of claim 11, wherein the three-dimensional image comprises a volumetric image, and the method includes estimating a local tracking parameter from the volumetric image at the indicated position in response to the user indicating the position.

13. A non-transitory computer readable medium that includes a program that, when executed by a processor, causes the processor to:
    display, on a display device, a three-dimensional image representing at least a tubular structure;
    enable a user to indicate a position on a vessel of the tubular structure displayed on the display device to provide an indicated position; and
    identifying, by a processing system, a portion of the tubular structure situated around the indicated position,
    wherein the identified portion of the tubular structure includes bifurcations, if any bifurcations exist in the portion, and extends up to a predefined distance measure from the indicated position without further user input, the predefined distance measure being independent of the image and the indicated position.

14. The medium of claim 13, wherein the program causes the processor to display a graphical annotation in the displayed three-dimensional image, indicative of the identified portion of the tubular structure.

15. The medium of claim 13, wherein the program causes the processor to measure the predefined distance measure along the tubular structure.

16. The medium of claim 15, wherein the program causes the processor to measure a length of the tracked vessel from the indicated position along the tubular structure.

17. The medium of claim 15, wherein the program causes the processor to count a number of bifurcations encountered from the indicated position along the tubular structure.

18. The medium of claim 13, wherein the program causes the processor to provide a multi-curved reformat following the curvature of at least a part of a vessel from the indicated position up to and beyond a bifurcation of the tubular structure, and following the curvature of at least part of two vessels beyond the bifurcation.

19. The medium of claim 13, wherein the three-dimensional image comprises a volumetric image, and the program causes the processor to estimate a local tracking parameter from the volumetric image at the indicated position in response to the user indicating the position.

20. The medium of claim 13, wherein the program causes the processor to compute a weighted average of an element of a structure tensor, the weighted average being computed over a region with a given size around the indicated position.

* * * * *